US012016773B2

(12) United States Patent
McDonald et al.

(10) Patent No.: US 12,016,773 B2
(45) Date of Patent: Jun. 25, 2024

(54) HEART REPLACEMENT VALVE WITH LEAFLET INVERSION AND REPLACEMENT PROCEDURE OF A HEART VALVE

(71) Applicants: Michael B. McDonald, Cordova, TN (US); Vinayak Bapat, Minneapolis, MN (US)

(72) Inventors: Michael B. McDonald, Cordova, TN (US); Vinayak Bapat, Minneapolis, MN (US)

( * ) Notice: Subject to any disclaimer, the term of this patent is extended or adjusted under 35 U.S.C. 154(b) by 130 days.

(21) Appl. No.: 17/468,325

(22) Filed: Sep. 7, 2021

(65) Prior Publication Data
US 2022/0071764 A1 Mar. 10, 2022

Related U.S. Application Data

(60) Provisional application No. 63/074,860, filed on Sep. 4, 2020.

(51) Int. Cl.
*A61F 2/24* (2006.01)
*A61B 17/32* (2006.01)

(52) U.S. Cl.
CPC ............ *A61F 2/2433* (2013.01); *A61B 17/32* (2013.01); *A61F 2/2418* (2013.01); *A61B 2017/320052* (2013.01); *A61F 2220/0041* (2013.01)

(58) Field of Classification Search
CPC ...... A61F 2/95; A61F 2/07; A61F 2002/9665; A61F 2002/9511; A61F 2/90; A61F 2/2418; A61F 2/954; A61F 2002/9505; A61F 2/9522; A61F 2/86; A61F 2/2439; A61F 2/243; A61F 2/242; A61F 2/2412; A61F 2/2436; A61F 2/2409; A61F 2/2427; A61F 2/02; A61F 2/82; A61F 2/89; A61F 2/24; A61F 2/2466; A61F 2/06; A61F 2220/0025; A61F 2002/9528; A61F 2002/9534; A61F 2220/0091; A61F 2/011; A61F 2250/0048; A61F 2250/0029; A61F 2250/0018
See application file for complete search history.

(56) References Cited

U.S. PATENT DOCUMENTS

| | | | | |
|---|---|---|---|---|
| 9,180,005 | B1 * | 11/2015 | Lashinski | A61M 25/0152 |
| 9,393,115 | B2 * | 7/2016 | Tabor | A61F 2/2436 |
| 9,566,178 | B2 * | 2/2017 | Cartledge | A61F 2/966 |
| 9,750,603 | B2 * | 9/2017 | Bell | A61F 2/2418 |
| 9,848,983 | B2 * | 12/2017 | Lashinski | A61F 2/2409 |
| 9,907,681 | B2 * | 3/2018 | Tobis | A61B 17/0401 |
| 10,278,820 | B2 * | 5/2019 | Bar | A61F 2/2445 |
| 11,185,405 | B2 * | 11/2021 | Girard | A61F 2/2469 |
| 11,197,754 | B2 * | 12/2021 | Saffari | A61F 2/2418 |
| 11,337,800 | B2 * | 5/2022 | Schreck | A61F 2/2418 |
| 11,357,624 | B2 * | 6/2022 | Guyenot | A61F 2/2442 |

(Continued)

*Primary Examiner* — Seema Mathew
(74) *Attorney, Agent, or Firm* — Jonathan Pierce; Pierre Campanac; Porter Hedges LLP

(57) ABSTRACT

A procedure for placing a cardiac valve includes cutting leaflets of another cardiac valve, expanding the cardiac valve, applying a downward pushing force to the expanded cardiac valve, and inverting the cut leaflets of the other cardiac valve toward a ventricle. The cardiac valve includes a self-expanding frame, vertical posts coupled to the self-expanding frame, and valve leaflets coupled to the self-expanding frame or to the vertical posts. Each of the vertical posts includes a connection to a corresponding control wire.

16 Claims, 3 Drawing Sheets

(56) References Cited

U.S. PATENT DOCUMENTS

| | | | |
|---|---|---|---|
| 11,523,905 B2* | 12/2022 | Griswold | A61F 2/2466 |
| 11,589,981 B2* | 2/2023 | Girard | A61F 2/2412 |
| 11,737,876 B2* | 8/2023 | Anderson | A61F 2/2466 623/2.11 |
| 2002/0161377 A1* | 10/2002 | Rabkin | A61B 17/221 623/1.11 |
| 2004/0186565 A1* | 9/2004 | Schreck | A61F 2/2427 623/2.38 |
| 2004/0260394 A1* | 12/2004 | Douk | A61F 2/2433 606/153 |
| 2005/0137686 A1* | 6/2005 | Salahieh | A61F 2/2439 623/2.11 |
| 2005/0137699 A1* | 6/2005 | Salahieh | A61F 2/2418 623/2.11 |
| 2007/0088431 A1* | 4/2007 | Bourang | A61F 2/2436 623/2.11 |
| 2007/0203503 A1* | 8/2007 | Salahieh | A61F 2/2436 623/2.11 |
| 2008/0195199 A1* | 8/2008 | Kheradvar | A61F 2/2418 623/2.11 |
| 2010/0152838 A1* | 6/2010 | Kang | A61F 2/2418 623/1.36 |
| 2010/0249920 A1* | 9/2010 | Bolling | A61F 2/2445 623/2.11 |
| 2011/0224785 A1* | 9/2011 | Hacohen | A61F 2/2457 623/2.18 |
| 2011/0264191 A1* | 10/2011 | Rothstein | A61F 2/2418 623/1.11 |
| 2011/0288632 A1* | 11/2011 | White | A61F 2/243 29/428 |
| 2012/0022640 A1* | 1/2012 | Gross | A61F 2/2427 623/2.11 |
| 2013/0046373 A1* | 2/2013 | Cartledge | A61F 2/966 623/1.11 |
| 2013/0150956 A1* | 6/2013 | Yohanan | A61F 2/2418 623/2.14 |
| 2013/0310923 A1* | 11/2013 | Kheradvar | A61B 8/0841 623/2.11 |
| 2014/0121763 A1* | 5/2014 | Duffy | A61F 2/2457 623/2.11 |
| 2016/0158003 A1* | 6/2016 | Wallace | A61F 2/24 623/2.17 |
| 2016/0213467 A1* | 7/2016 | Backus | A61F 2/2409 |
| 2016/0220365 A1* | 8/2016 | Backus | A61F 2/2415 |
| 2016/0367360 A1* | 12/2016 | Cartledge | A61F 2/2436 |
| 2017/0042671 A1* | 2/2017 | Backus | A61F 2/2409 |
| 2017/0049563 A1* | 2/2017 | Straubinger | A61F 2/2409 |
| 2017/0128198 A1* | 5/2017 | Cartledge | A61F 2/2436 |
| 2017/0231765 A1* | 8/2017 | Desrosiers | A61F 2/2418 623/2.11 |
| 2017/0325951 A1* | 11/2017 | Escalona | A61F 2/2436 |
| 2018/0325665 A1* | 11/2018 | Gurovich | A61F 2/2418 |
| 2020/0000590 A1* | 1/2020 | Salahieh | A61F 2/2409 |
| 2020/0188099 A1* | 6/2020 | Dvorsky | A61F 2/9517 |
| 2020/0360134 A1* | 11/2020 | Peterson | A61F 2/90 |

* cited by examiner

HEART REPLACEMENT VALVE WITH LEAFLET INVERSION AND REPLACEMENT PROCEDURE OF A HEART VALVE

CROSS-REFERENCE TO RELATED APPLICATIONS

This application claims the benefit of priority to U.S. provisional application Ser. No. 63/074,860 filed on Sep. 4, 2020, which is incorporated herein by reference for all or any purposes.

BACKGROUND

The age of transcatheter aortic valve replacement started in 1985. Since then, hundreds of thousands of valves have been placed by the transcatheter approach. As these valves age and eventually fail, they will need to be replaced. One of the evolving challenges in the medical field of structural heart is the ability to place a transcatheter heart valve inside a previously placed cardiac valve.

Furthermore, the placement of a transcatheter valve inside even a native valve can be, at times, challenging due to cardiac anatomy.

Often the major obstacle is the displacement of the existing valve leaflets to a position obstructing the origin of the coronary arteries. Obstruction of coronary blood flow can be rapidly catastrophic. Valve leaflets blocking or even partially blocking coronary catheter access can likewise have dire consequences for the patient.

The present options to alleviate this valve leaflet problem have been very limited, difficult, and with substantial risk to the patient.

BRIEF SUMMARY OF THE DISCLOSURE

A valve cutter provides a percutaneous option for making cuts in the original leaflets of an existing cardiac valve, which may be an artificial or native valve. Longitudinal cuts in the valve leaflets open up a path for both blood flow and catheter access into the coronary arteries.

A replacement procedure includes two main steps: the cutting of the original leaflets of the existing aortic valve and the placement of a replacement valve within the native or previously placed aortic valve. Percutaneous vascular access is first obtained. This access is usually via the femoral artery with a large bore sheath. A guidewire is placed from the sheath across the aortic valve into the left ventricle. Over the guidewire, the valve cutter is loaded and advanced into the aortic valve. Vertical cuts are made in the three leaflets of the aortic valve. The valve cutter is then exchanged over the guidewire for the replacement valve. This replacement valve is advanced over the guidewire until it is positioned inside the existing aortic valve. The replacement valve is then deployed inside the existing valve.

A replacement valve is specifically designed for the replacement procedure of an existing valve. The replacement valve is placed from percutaneous access. The basic structure of the replacement valve is a self-expanding nitinol frame. The replacement valve is compressed on a delivery catheter and expanded with the retraction of an outer sheath. Three control wires with a self-releasing or screw connection tether the replacement valve to the valve delivery catheter.

The replacement procedure with leaflet inversion opens up an access window where the original leaflets would normally obstruct blood flow and catheter access to the coronary arteries. This procedure involves making one or more longitudinal cuts in some or each of the original leaflets. Once the original leaflets are cut, the replacement valve can be placed within the existing valve. The replacement valve is then positioned just above the existing valve. The leaflet commissures of the replacement valve and the existing valve are aligned. The replacement valve is allowed to expand to a point of close proximity or lightly touching the inner margins of the existing valve. The replacement valve is then pushed down into the existing valve. When the replacement valve is pushed down into the existing valve, the original leaflets, which are cut, are moved inferiorly toward the left ventricle. This maneuver opens up windows in the existing valve that are free from leaflet blockage. If the existing valve is a transcatheter valve, the windows are where the cut leaflets are pushed away from the sides of the existing valve, and are no longer against the frame (or wall) of the existing valve. In some biological surgical valves, the windows are where the cut leaflets are pushed away from the coronary ostium. These unobstructed windows allow coronary blood flow and catheter access. The inferior edge of the replacement valve is positioned at or just slightly beyond the inferior edge of the existing valve. At this point, x-ray dye can be injected just above the valves to confirm free blood flow into the coronary arteries and proper position of the replacement valve. If the position is not ideal, the replacement valve can be recaptured within the sheath of the delivery catheter. A repeat positioning can then be done prior to full expansion and release of the replacement valve.

BRIEF DESCRIPTION OF THE DRAWINGS

For a more detailed description of the embodiments of the disclosure, reference will now be made to the accompanying drawings, wherein.

DETAILED DESCRIPTION

Figure 1:
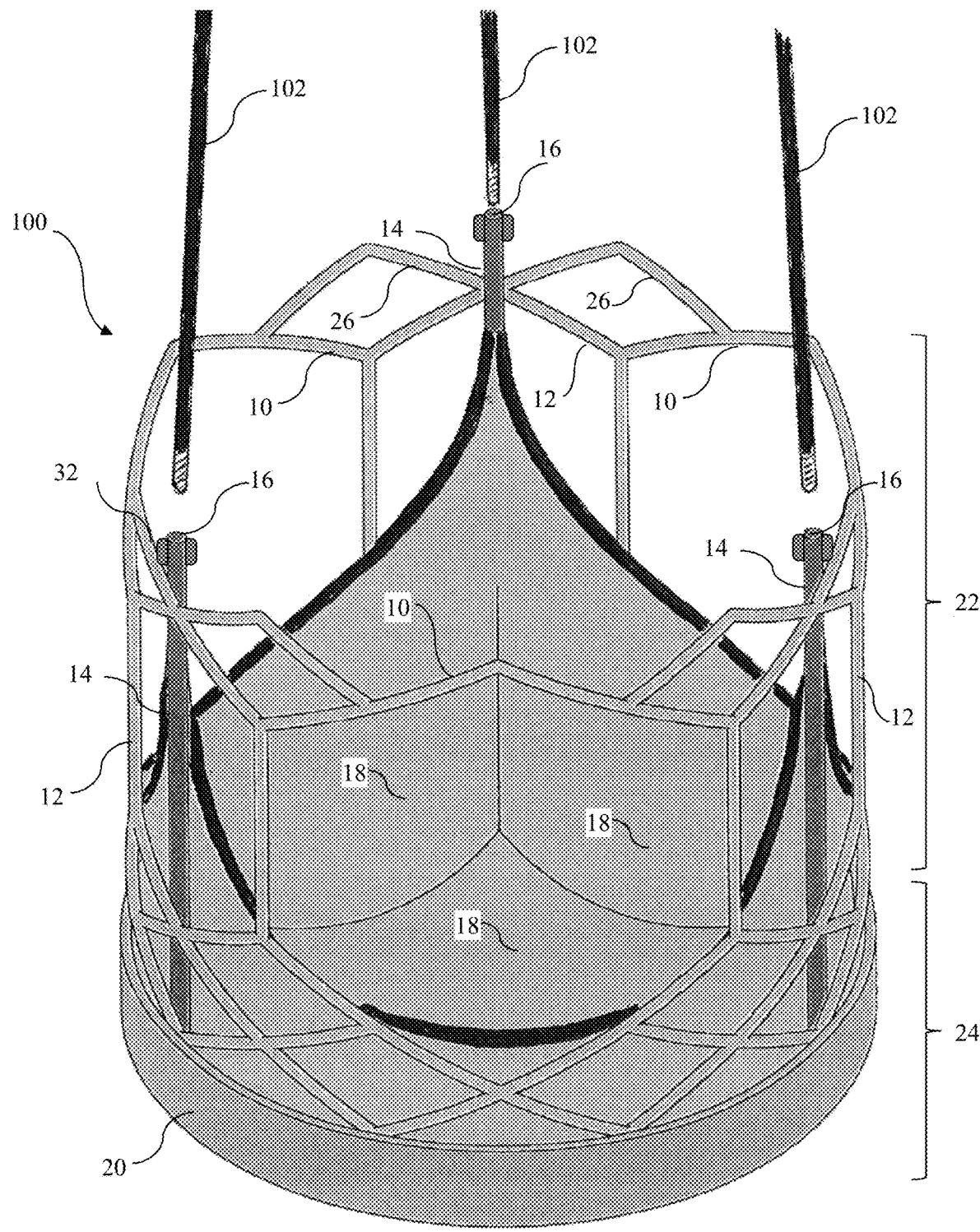
FIG. 1 is a perspective view of a replacement valve, illustrated expanded.

FIG. 1 illustrate an example embodiment of a replacement valve 100, when it is expanded. The replacement valve 100 is a low profile, self-expanding nitinol valve. In some preferred embodiments, the replacement valve 100 is designed to fit inside a previously placed cardiac valve. While this replacement valve 100 is tailored for the transcatheter valve-in-valve replacement procedures, the replacement valve 100 is also suited for transcatheter placement as a primary replacement valve.

The replacement valve 100 has several new design features that allow it to function in this new procedure.

The replacement valve 100 is designed with three large cells 10 and three medium cells 12 at the upper portion 22 of a nitinol frame. These cells 10, 12 may be open and shaped like hexagons. The large cells 10 minimize the difficulty in placing a catheter into the coronary arteries. Two of the large cells will be placed in front of, or aligned with, coronary artery ostium. The nitinol frame is made stiff by using heavy gauge nitinol. The nitinol frame allows compression of the original leaflets of the existing valve between the existing valve and the frame of the replacement valve 100.

Figure 2:
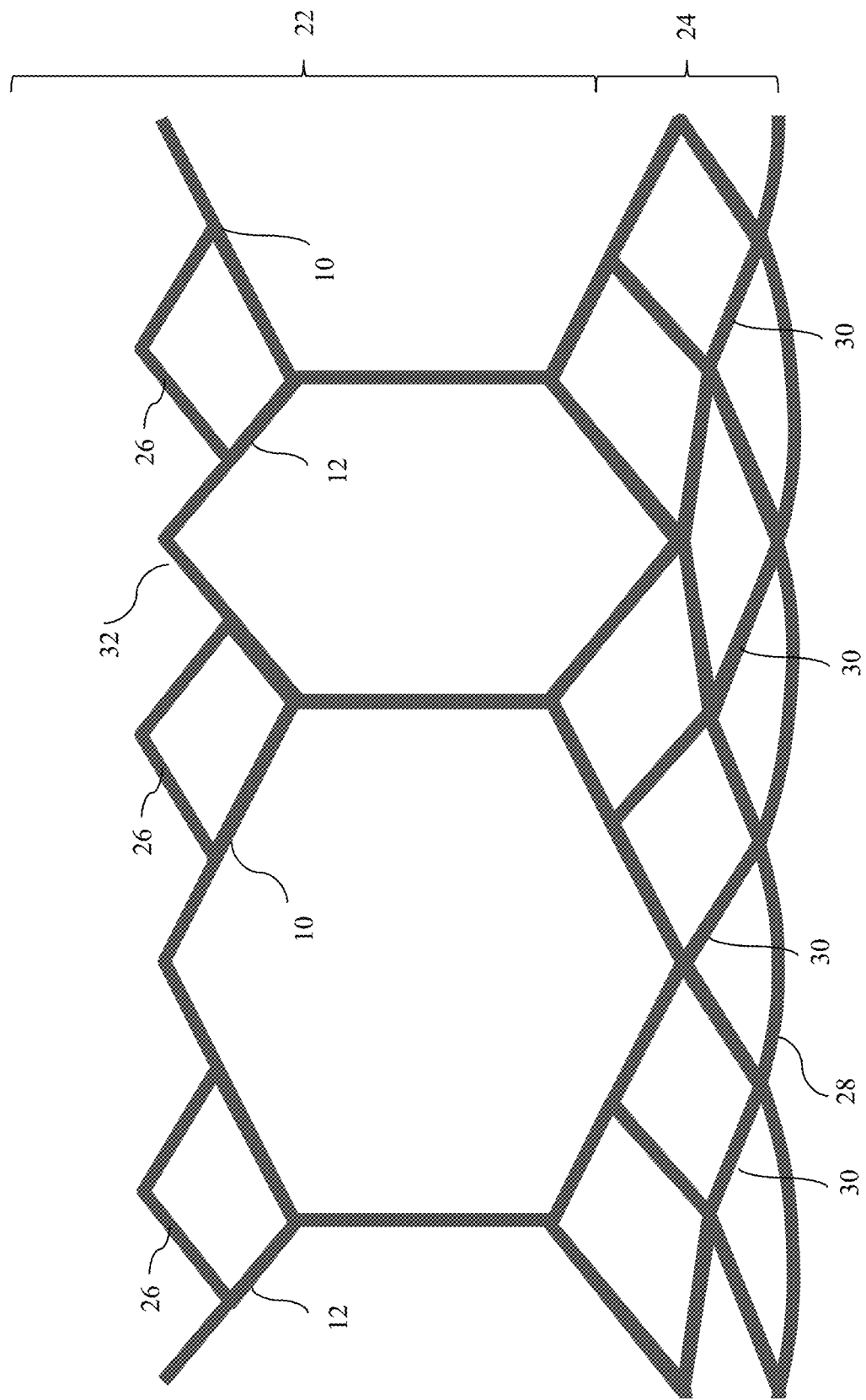
FIG. 2 is a flattened view of a portion of the nitinol frame of a replacement valve, illustrated expanded.

FIG. 2 illustrates a flattened view of a portion of the nitinol frame of the valve 100, when it is expanded. The inferior edge 28 of the frame is flat or nearly flat when the valve 100 is fully expanded. This configuration is to avoid having points that could snag on the leaflets of the existing valve when the replacement valve 100 is pushed down and inverting the original valve's leaflets.

The inferior edge 28 of the nitinol frame may or may not be covered with a fabric skirt 20 (shown in FIG. 1 only). The skirt 20 can aid slipping the replacement valve 100 inferiorly along the leaflets of the existing valve. The skirt can also help with sealing off any blood flow between the replacement and existing valves. The skirt 20 may be slightly more prominent in enter area between the commissures between leaflets 18.

The inferior edge 28 of the nitinol frame is engineered with several new design features. The arm length of the bottom half of the inferior row 30 of cells, which may be shaped like diamonds, is shorter than the arm length in the upper half of the cell. This cell arm length differential results in a flat or nearly flat inferior edge 28 when the replacement valve 100 is fully expanded.

The lower tip at the intersection of the two shorter arms on the inferior edge 28 of the replacement valve 100 is rounded out so that when the replacement valve 100 is expanded, a smooth bump and not a corner point is created. The leading nitinol edges on the bottom portion 24 of the nitinol frame are smooth and present a decreased sliding resistance when pushing down on the original leaflets of the existing valve.

Referring back to FIG. 1, the cells 26 of the nitinol frame at the top of the valve, that is, the top rim cells that are illustrated shaped like diamonds, may have a slight inward angle. The inward angle is to help with the recapture of the replacement valve 100 with the delivery catheter sheath when needed.

The height of the replacement valve 100 is less than the height of most of the presently used self-expanding valves. This replacement valve 100 can extend over an area that only covers the inner length of the existing valve in the aortic annular area. The surgical biologic valves and balloon deployed transcatheter valves have a lower height than self-expanding valves. The height of the replacement valve 100 is nevertheless sufficient for use with a surgical biologic valve and balloon. There can be various sizes of the replacement valve 100. The sizes can vary in diameter and height.

Another feature to this replacement valve 100 is three vertical posts 14 that extend from the inferior edge 28 (illustrated in FIG. 2) of the valve, or close to the inferior edge 28 of the replacement valve 100, to beyond the top edge 32. These posts 14 give the valve the vertical strength that is needed when the valve is pushed down into the existing valve, whose leaflets have been cut. This downward force is needed to invert the cut leaflets in the direction of the left ventricle.

The three vertical posts 14 are where the valve delivery wires 102 attach to the replacement valve 100. At the top end 16 of the vertical posts 14, the diameter may be slightly increased in a pod-like configuration. This localized increased diameter will not only strengthen the joint, but aid in valve recapture by the sheath. In other embodiments, the top ends of the vertical posts may be flush with the top rim of the valve.

Figure 3:
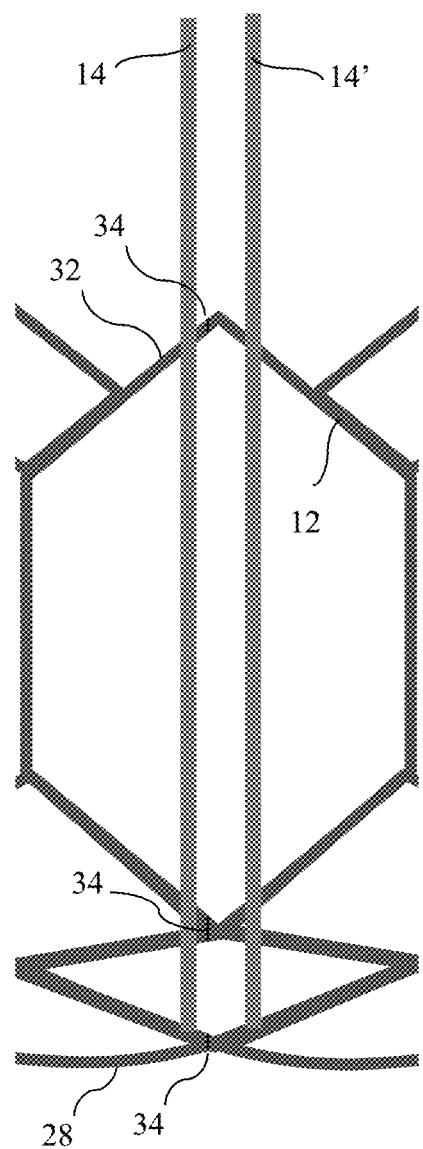
FIG. 3 is a flattened view of a portion of the nitinol frame of a replacement valve having a fracture feature.

FIG. 3 illustrates a flattened view of a portion of a nitinol frame of a replacement valve. Another design feature of this replacement valve is to have a fracture feature. This fracture feature allows vertical fracturing of the valve frame when the frame is dilated, typically, with a high pressure balloon. This fracture feature may include an additional vertical post 14' that is parallel to one of the three vertical posts 14 that connect to the valve delivery wires. There is a slight gap (e.g., in the range of 2 mm) between the additional vertical post 14' and the one of the three vertical posts 14. The nitinol frame that is located within this gap is notched (see notches 34) to allow splitting of the frame at this point when the valve is subjected to balloon dilatation caused by high inflation pressure, for example, in the range of 10 to 20 atm. The purpose of a valve fracture feature is to allow the placement of a larger sized second valve within the replacement valve 100 if needed in the future.

The replacement valves and the replacement procedures with leaflet inversion described herein provide a new and novel way to overcome the problem of the valve leaflet obstruction of coronary blood flow and obstruction of catheter access in the aortic valve. These replacement valves and replacement procedures with leaflet inversion offer a relatively simple solution to a pressing and complex problem that is now present in the structural heart field of cardiology. It is believed that by using the valve cutter along with the specifically designed replacement valves described herein, the leaflet-coronary obstruction problem can be resolved in most cases.

Specific embodiments of the invention are shown by way of example in the drawings and description. It should be understood, however, that the drawings and detailed description thereto are not intended to limit the claims to the particular form disclosed, but on the contrary, the intention is to cover all modifications, equivalents, and alternatives falling within the scope of the claims.

What is claimed is:

1. A system for placing a cardiac valve, comprising:
    the cardiac valve including:
        a self-expanding frame including a plurality of open cells delineated by arms, the self-expanding frame having a lower portion extending upward from an inferior edge of the self-expanding frame, the self-expanding frame having an upper portion extending downward from a top edge of the self-expanding frame, wherein the upper portion includes arms that are the longest in the self-expanding frame, the arms delineating open cells that are the largest in the self-expanding frame;
        a plurality of vertical posts coupled to the self-expanding frame, each of the plurality of vertical posts having a lower end located along the lower portion of the self-expanding frame, each of the plurality of vertical posts including a connection to a corresponding one of a plurality of control wires; and
        valve leaflets coupled to the self-expanding frame or to one or more of the plurality of vertical posts,
    wherein the plurality of vertical posts are configured to have, collectively, a strength sufficient for supporting, when the cardiac valve is expanded, a downward pushing force necessary for inverting cut leaflets of another cardiac valve toward a ventricle, and
    wherein the open cells in the lower portion are configured to have a stiffness sufficient to compress cut leaflets of another cardiac valve radially against the other cardiac valve.

2. The system of claim 1 further comprising the plurality of control wires.

3. The system of claim 2 wherein at least one connection to one of the plurality of control wires includes a screw connection or a self-releasing connection.

4. The system of claim 2 wherein a diameter of each of the plurality of vertical posts is larger at the top end.

5. A system for placing a cardiac valve, comprising:
the cardiac valve including:
a frame including a plurality of open cells delineated by arms, the frame having a lower portion extending upward from an inferior edge of the frame, the frame having an upper portion extending downward from a top edge of the frame;
a plurality of vertical posts coupled to the frame, each of the plurality of vertical posts having a lower end located along the lower portion of the frame, each of the plurality of vertical posts including a connection to a corresponding one of a plurality of control wires; and
valve leaflets coupled to the frame or to one or more of the plurality of vertical posts wherein the plurality of vertical posts are configured to have, collectively, a strength sufficient for supporting, when the cardiac valve is expanded, a downward pushing force necessary for inverting cut leaflets of another cardiac valve toward a ventricle,
wherein the lowermost row of open cells includes a first plurality of arms forming the inferior edge of the frame and a second plurality of arms distinct from the first plurality, and
wherein the first plurality of arms includes arms that are shorter than each arm of the second plurality of arms,
whereby the inferior edge of the frame is sufficiently flat when the cardiac valve is expanded to avoid catching a cut leaflet of another cardiac valve.

6. The system of claim 5 wherein the upper portion includes arms that are the longest in the frame, the arms delineating open cells that are the largest in the frame.

7. The system of claim 5 wherein the frame includes notches,
wherein the notches are configured to fracture when the cardiac valve is expanded with a balloon, and
wherein the notches are configured to split the frame when the notches are fractured.

8. The system of claim 5 wherein each of the plurality of vertical posts has an upper end located above the top edge of the frame.

9. A method of placing a cardiac valve, comprising:
cutting leaflets of another cardiac valve;
expanding the cardiac valve;
applying a downward pushing force to the expanded cardiac valve;
inverting the cut leaflets of the other cardiac valve toward a ventricle; and compressing the cut leaflets radially against the other cardiac valve,
wherein the cardiac valve includes:
a self-expanding frame including a plurality of open cells delineated by arms, the self-expanding frame having a lower portion extending upward from an inferior edge of the self-expanding frame, the self-expanding frame having an upper portion extending downward from a top edge of the self-expanding frame, wherein the upper portion includes arms that are the longest in the self-expanding frame, the arms delineating open cells that are the largest in the self-expanding frame;
a plurality of vertical posts coupled to the self-expanding frame, each of the plurality of vertical posts having a lower end located along the lower portion of the self-expanding frame, each of the plurality of vertical posts including a connection to a corresponding one of a plurality of control wires; and
valve leaflets coupled to the self-expanding frame or to one or more of the plurality of vertical posts,
wherein the plurality of vertical posts are configured to have, collectively, a strength sufficient for supporting, when the cardiac valve is expanded, a downward pushing force necessary for inverting cut leaflets of another cardiac valve toward a ventricle, and
wherein the open cells in the lower portion are configured to have a stiffness sufficient to compress cut leaflets of another cardiac valve radially against the other cardiac valve.

10. The method of claim 9 further comprising releasing each connection to each of the plurality of control wires,
wherein at least one connection to one of the plurality of control wires includes a screw connection or a self-releasing connection.

11. The method of claim 9 wherein a diameter of each of the plurality of vertical posts is larger at the top end.

12. A method of placing a cardiac valve, comprising:
wherein the cardiac valve includes:
a frame including a plurality of open cells delineated by arms, the frame having a lower portion extending upward from an inferior edge of the frame, the frame having an upper portion extending downward from a top edge of the frame;
a plurality of vertical posts coupled to the frame, each of the plurality of vertical posts having a lower end located along the lower portion of the frame, each of the plurality of vertical posts including a connection to a corresponding one of a plurality of control wires; and
valve leaflets coupled to the frame or to the vertical posts,
wherein the plurality of vertical posts are configured to have, collectively, a strength sufficient for supporting, when the cardiac valve is expanded, a downward pushing force necessary for inverting cut leaflets of another cardiac valve toward a ventricle,
wherein the lowermost row of open cells includes a first plurality of arms forming the inferior edge of the frame and a second plurality of arms distinct from the first plurality, and
wherein the first plurality of arms includes arms that are shorter than each arm of the second plurality of arms,
whereby the inferior edge of the frame is sufficiently flat when the cardiac valve is expanded to avoid catching a cut leaflet of another cardiac valve;
the method comprising:
cutting leaflets of another cardiac valve;
expanding the cardiac valve, wherein expanding the cardiac valve causes the inferior edge of the frame to be sufficiently flat to avoid catching one of the cut leaflets of the other cardiac valve;
applying a downward pushing force to the expanded cardiac valve; and
inverting the cut leaflets of the other cardiac valve toward a ventricle.

13. The method of claim 12 further comprising aligning open cells that are the largest in the frame with a coronary artery ostium,
wherein the upper portion includes arms that are the longest in the frame, the arms delineating the open cells that are the largest in the frame.

14. The method of claim 12 further comprising:
expanding the cardiac valve with a balloon;
fracturing notches included in the frame;
splitting the frame; and placing a larger-sized cardiac valve within the cardiac valve.

15. The method of claim 12 wherein the other cardiac valve is a surgical biologic valve, a balloon deployed transcatheter valve, or a self-expanding valve.

16. The method of claim 15 wherein a height of the other cardiac valve is less than a height of the cardiac valve.

* * * * *